United States Patent [19]

Karle et al.

[11] Patent Number: 4,461,837
[45] Date of Patent: Jul. 24, 1984

[54] CONTAMINATION-FREE STERILIZATION INDICATING SYSTEM

[75] Inventors: David A. Karle, McKean; Raymond C. Kralovic, North Springfield, both of Pa.

[73] Assignee: American Sterilizer Company, Erie, Pa.

[21] Appl. No.: 306,945

[22] Filed: Sep. 30, 1981

[51] Int. Cl.³ .................. C12M 1/24; C12M 1/16; C12M 1/18; C12Q 1/22

[52] U.S. Cl. .................. 435/296; 435/31; 435/299; 435/300; 435/810

[58] Field of Search ............ 435/31, 296, 299, 300, 435/810; 206/219, 222; 215/227, DIG. 8

[56] References Cited

U.S. PATENT DOCUMENTS

| | | | |
|---|---|---|---|
| 2,287,746 | 6/1942 | Morton | 435/296 X |
| 2,642,065 | 6/1953 | Negri | 206/222 X |
| 2,954,144 | 9/1960 | Elam et al. | 206/222 X |
| 3,240,391 | 3/1966 | Garton | 206/222 X |
| 3,297,184 | 1/1967 | Andelin | 435/296 X |
| 3,327,710 | 6/1967 | Freeberg et al. | 206/222 X |
| 3,451,894 | 6/1969 | Anandam | 435/801 X |
| 3,616,263 | 10/1971 | Anandam | 435/296 |
| 3,655,035 | 4/1972 | Mühlbauer | 206/219 |
| 3,661,717 | 5/1972 | Nelson | 435/31 |
| 3,739,947 | 6/1973 | Baumann et al. | 206/219 X |
| 3,762,540 | 10/1973 | Baumann et al. | 206/219 |
| 4,304,869 | 12/1981 | Dyke | 435/296 |

Primary Examiner—Robert J. Warden
Attorney, Agent, or Firm—Robert D. Yeager; Andrew J. Cornelius

[57] ABSTRACT

A biological system for use in sterilization processes. The system contains a container having test spores and a growth medium therein and means for bringing the medium into effective contact with the spores. The container includes a closure providing a tortuous path from the exterior to the interior of the container.

1 Claim, 4 Drawing Figures

CONTAMINATION-FREE STERILIZATION INDICATING SYSTEM

BACKGROUND OF THE INVENTION

1. Field of the Invention

This invention relates to a system for monitoring the efficacy of a process of sterilization in a manner that prevents the contaminating effect of airborne microorganisms and that permits incubation of test spores without culture media loss.

2. Description of the Prior Art

In the field of sterilization of articles, it is desirable to ascertain whether a particular load of articles that is subjected to a sterilizing environment, either steam or gas, has in fact been exposed to an environment which would have killed microorganisms at an acceptable rate. This objective may be carried out in a variety of ways but generally involves subjecting a known number of test spores to the same sterilizing environment, under the same conditions, as that to which the articles in the sterilizer are subjected. Upon completion of the sterilization cycle, the test spores are removed from the sterilizer and are exposed to a growth-inducing medium. The test spores so exposed are incubated for a specified time period and then are checked for spore growth. If no microbiological growth occurs, it can be assumed that the articles in the particular load tested are "sterile" for their intended purpose. If, on the other hand, growth is observed, the articles may not be deemed "sterile" and should be subjected to a completely new sterilization cycle.

In order to guarantee the accuracy of the test just described, it is, of course, necessary that the test spores be exposed to the sterilizing environment within the sterilizer; this means that the container used for the test spores must be open to the surrounding atmosphere. But after the sterilization cycle is complete and the sterilizer is opened, the test container must be removed from the sterilizer and thereby is subjected to a nonsterile environment while the manipulations required to bring the spores into contact with the growth medium are carried out. During this period, airborne microorganisms present in the environment may be introduced into the test container and render the subsequent sterilization tests unreliable.

Workers in the art have recognized this problem and their efforts to remedy it generally have centered around providing some sort of shielding means around the test container, such as a membrane or filter that generally is penetrable by sterilant but is impenetrable by airborne microorganisms; see, e.g., U.S. Pat. Nos. 3,661,717 and 3,440,144. The existence of any barrier to the free flow of sterilizing environment to the test spores during sterilization, however, may cast doubt upon the validity of the sterilization test.

Further, the known biological indicating systems suffer an additional disadvantage relating to the required incubation period. Because the known systems are constructed at least in part of materials that are permeable to the sterilizing environment, they are subject to media loss through evaporation when the test container is subjected to incubation temperatures. This problem is solved in the known systems by the use of special incubation equipment in which the humidity and thus media evaporation rates are reduced. However, the introduction of water vapor into an enclosure containing the test system offers an opportunity for extraneous contamination of the test components because the test container is not sealed during the incubation period.

SUMMARY OF THE INVENTION

The present invention seeks to overcome the problems associated with prior art sterilization indicating systems by providing a system that assures unobstructed access to the test spores by the sterilizing environment during sterilization and that, following removal of the test container from the sterilizer, prevents access to the test spores by airborne microorganisms present in the surrounding nonsterile environment.

The invention also eliminates the loss of water vapor by evaporation of the culture medium because the invention provides means for sealing the test container when the indicating system is activated.

The present invention provides a biological indicating system for use in sterilization processes comprising: a container having access means for providing a path of unobstructed fluid communication between the interior of the container and the surrounding environment outside; test spores present within the container; a medium adapted to induce, with incubation, growth of the spores, the medium being present in the container but out of effective contact with the spores; a closure for the container access means, the closure being movable with respect to the access means from a first position, wherein the path of fluid communication to the interior of the container is a tortuous path defined by a portion of the body of the container and a portion of the body of the closure, and a second position, wherein the path of fluid communication to the interior of the container is blocked by a sealing engagement between portions of the closure and portions of the container; and means for bringing the medium into effective contact with the spores.

In a preferred embodiment of the invention, effective contact between the medium and the spores occurs upon movement of the closure from its first position to its second position.

Other features and advantages of the present invention will become apparent from the following detailed description, taken with the accompanying drawings.

DESCRIPTION OF THE PREFERRED EMBODIMENTS

Figure 1:
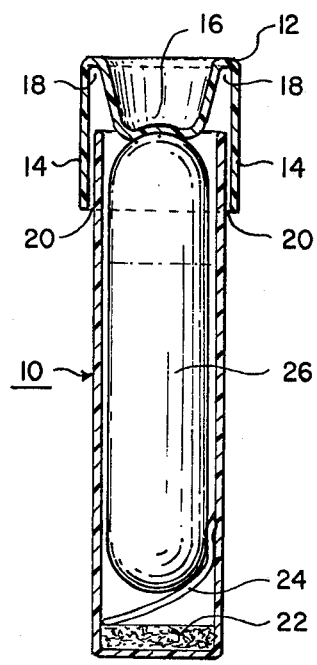
FIG. 1 is a front elevation view, partly in section, of one embodiment of a test spore container and its closure prior to activation of the system of the present invention.
Figure 2:
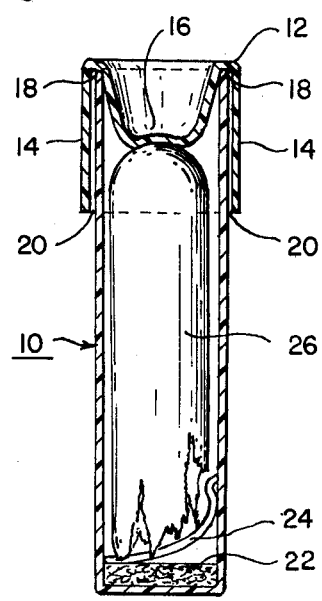
FIG. 2 is a view of the embodiment of FIG. 1 after activation of the system of the present invention.

Referring to the drawings, particularly to FIGS. 1 and 2, there is shown a biological indicator system for use in sterilization processes constructed in accordance with the present invention. The system includes a transparent, hollow, cylindrical container 10, preferably formed of rigid plastic having a closed bottom end and an open top. A cap 12, having cylindrical sidewalls 14, is employed as a closure for the open end of container 10. The top of cap 12 has an inwardly extending central recessed portion 16 which upon formation results in the formation of a circular groove 18 bounded by the wall of recessed portion 16 and sidewalls 14 of cap 12. Cap 12 is dimensioned to provide an annular space 20 between the outer walls of container 10 and the inner surface of sidewalls 14 of cap 12.

Disposed within container 10 are a strip of test spores 22, a breaking wire 24 and a frangible ampul 26. Spore strip 22 contains viable bacterial spores of known resistance. Ampul 26 contains a liquid nutrient medium such as a broth for inducing growth of the spores on strip 22 upon incubation; preferably, ampul 26 also contains a suitable dye for providing a visual indication of spore growth in accordance with chemical reactions well known in the art.

The components of the system of the present invention just described are dimensioned to permit recessed portion 16 of cap 12 to rest on the top of ampul 26. In this position, fluid communication is established between the exterior of container 10 and its interior through annular space 20 and the open top end of container 10. This path of fluid communication is tortuous in that any matter traversing the path must negotiate at least two 90° bends to enter the interior of container 10.

The system of the present invention is used in sterilization processes by placing container 10, carrying its components and having cap 12 positioned as shown in FIG. 1, into a sterilizer along with a load of articles to be sterilized. During the sterilization cycle, sterilizing environment has free access to the interior of container 10 through annular space 20 and the open end of container 10. That environment has no difficulty negotiating the tortuous path provided by that path of fluid communication because of the varying pressure conditions that are normally present within the sterilizer during a given cycle. For example, under conditions of elevated pressure within the sterilizer, sterilizing environment will be forced into the interior of container 10 and thus into contact with spore strip 22.

Upon completion of the sterilizing cycle, container 10 is removed from the sterilizer and thereby is exposed to a nonsterile environment which may contain airborne microorganisms. Because there will be little or no pressure differential between the exterior and the interior of container 10, there is little tendency for the nonsterile environment, e.g. air, to flow into the interior of container 10, carrying with it airborne microorganisms. Access to the interior of container 10 by airborne microorganisms may be gained only by the microorganisms negotiating the tortuous path of fluid communication provided by cap 12 and the upper structure of container 10; such migration will be minimal because the microorganisms are incapable of independent movement.

Accordingly, spore strip 22 will not be contaminated by the nonsterile environment to which container 10 is exposed before the indicator system of the present invention can be activated. Referring to FIG. 2, such activation is brought about by the operator applying downward pressure on cap 12; this pressure is transferred to ampul 26 through recessed portion 16 and the compressive force created thereby between the sidewall of ampul 26 and breaking wire 24 is sufficient to rupture ampul 26 and permit its contents to contact spore strip 22. As the indicating system is activated in the manner just described, the upper rim of container 10 engages groove 18 in cap 12 and seals the interior of container 10. This sealing action assures that the spore growth test can proceed within container 10 without contamination from the outside environment and without loss of liquid from the culture medium due to evaporation.

Figure 3:
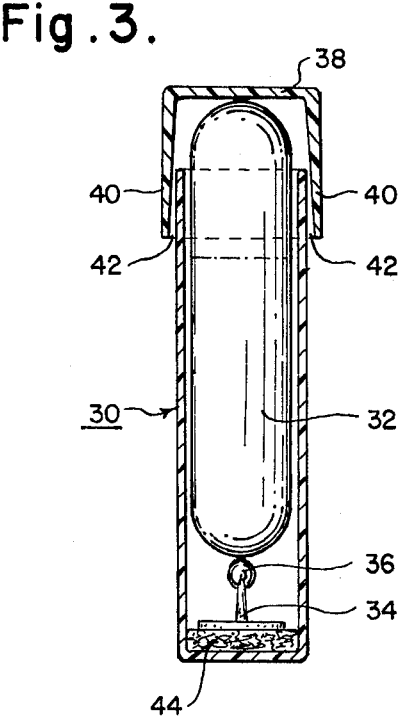
FIG. 3 is a front elevation view, partly in section, of a second embodiment of a test spore container and its closure prior to activation of the system of the present invention.
Figure 4:
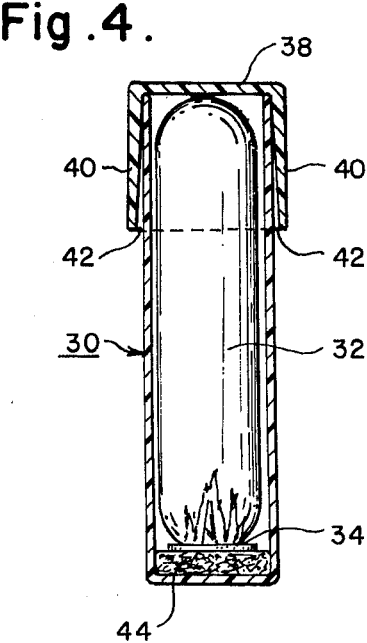
FIG. 4 is a view of the embodiment of FIG. 3 after activation of the system of the present invention.

An alternate embodiment of the present invention is shown in FIGS. 3-4. In that embodiment, container 30 houses ampul 32 which is supported within container 30 by a breaking device 34 that resembles a tack having a blunt-ended point 36. A cap 38 is supported over the top open end of container 30 by resting on the top of ampul 32. Cap 38 has sidewalls 40 that taper inwardly toward the flat top surface of cap 38, but when the cap is in the position shown in FIG. 3, an annular space 42 between sidewalls 40 and the upper outer surface of container 30 nevertheless is provided. Annular space 42 provides the path of fluid communication to the interior of container 30 in the same manner as the embodiment shown in FIGS. 1-2, but access to the interior of container 30 via that path can be gained only by a tortuous route.

Activation of the biological indicator carried within container 30 is accomplished by applying downward force on cap 38 sufficient to cause breaking device 34 to pierce the bottom end of ampul 32. The contents of ampul 32 thereby are brought into contact with spore strip 44. The tapered walls of cap 38 provide the necessary sealing action between it and container 30.

A further and particularly advantageous embodiment of the present invention is described in U.S. patent application Ser. No. 153,136, filed May 27, 1980, now U.S. Pat. No. 4,304,869, which is owned by the assignee hereof and which is hereby incorporated by reference herein.

The container of the present invention could be formed of a flexible material and be operated in the manner disclosed in U.S. Pat. No. 3,661,717, so long as the container is fitted with a closure that provides a tortuous path to the interior of the container and is capable of sealing the container.

What is claimed is:

1. A biological indicating system for use in sterilization processes comprising:
    a container having access means for providing a path of unobstructed fluid communication between the interior of said container and the surrounding environment outside;
    test spores present within said container;
    a medium adapted to induce growth of said spores, said medium being present in said container but out of effective contact with said spores;
    a closure for said container access means, said closure being movable with respect to said access means from a first position, wherein said path of fluid communication is a tortuous path defined by a portion of the body of said container and a portion of the body of said closure, and a second position, wherein said path of fluid communication is blocked by a sealing engagement between portions of said closure and portions of said container; and
    means for bringing said medium into effective contact with said spores said effective contact being initiated by the movement of said closure to said second position.

* * * * *